United States Patent
Naslund et al.

(10) Patent No.: US 7,417,239 B2
(45) Date of Patent: Aug. 26, 2008

(54) METHOD AND DEVICE FOR ELECTRON BEAM IRRADIATION

(75) Inventors: Lars Ake Naslund, Furulund (SE); Tommy Nilsson, Svedala (SE); Luca Poppi, Formigine (IT); Paolo Benedetti, Modena (IT); Anna Eriksson, Rydeback (SE); Filippo Ferrarini, Modena (IT)

(73) Assignee: Tetra Laval Holdings & Finance S.A., Pully (CH)

( * ) Notice: Subject to any disclaimer, the term of this patent is extended or adjusted under 35 U.S.C. 154(b) by 196 days.

(21) Appl. No.: 10/561,230

(22) PCT Filed: Jun. 8, 2004

(86) PCT No.: PCT/SE2004/000894

§ 371 (c)(1), (2), (4) Date: Dec. 19, 2005

(87) PCT Pub. No.: WO2004/110869

PCT Pub. Date: Dec. 23, 2004

(65) Prior Publication Data

US 2006/0145093 A1   Jul. 6, 2006

(30) Foreign Application Priority Data

Jun. 19, 2003 (SE) .................................. 0301781

(51) Int. Cl.
*G21G 5/00* (2006.01)

(52) U.S. Cl. ............. 250/492.1; 250/492.3; 250/455.11

(58) Field of Classification Search ............... 250/492.1
See application file for complete search history.

(56) References Cited

U.S. PATENT DOCUMENTS 3,790,801 A * 2/1974 Coleman ............... 250/453.11
4,035,981 A   7/1977 Braun et al.

(Continued)

FOREIGN PATENT DOCUMENTS

GB       1 353 831          5/1974

(Continued)

OTHER PUBLICATIONS

U.S. Appl. No. 10/555,759, filed Nov. 7, 2005.

*Primary Examiner*—David A. Vanore
*Assistant Examiner*—Phillip A. Johnston
(74) *Attorney, Agent, or Firm*—Buchanan, Ingersoll & Rooney PC

(57) ABSTRACT

The invention refers to a method and device for ventilating a device for electron beam irradiation of a web (W), the method comprising the steps of: providing a first chamber (107) comprising a web inlet opening (115) and a web outlet opening (115) and a web outlet opening (121), providing a second chamber (111) extending inside the first chamber (107), the second chamber (111) comprising a a web inlet opening (114), a web outlet opening (112), and an electron exit surface (21) through which electrons are adapted to be emitted into the second chamber (111), passing the web (W) through the second chamber (111), and creating a flow of a gaseous fluid through both the first and second chambers (107, 111) in a direction opposite the direction of travel of the web (W) by supplying said fluid into the web outlet opening (121) of the first chamber (107) and providing at least one outlet (113).

20 Claims, 5 Drawing Sheets

U.S. PATENT DOCUMENTS

| | | |
|---|---|---|
| 4,252,413 A | 2/1981 | Nablo |
| 5,194,742 A | 3/1993 | Avnery et al. |
| 5,473,164 A | 12/1995 | Klenert et al. |
| 6,426,507 B1 * | 7/2002 | Rangwalla et al. ....... 250/492.3 |
| 6,727,508 B1 * | 4/2004 | Tominaga et al. ........ 250/492.1 |
| 7,154,103 B2 * | 12/2006 | Koenck et al. ......... 250/455.11 |
| 2001/0035500 A1 | 11/2001 | Schianchi et al. |

FOREIGN PATENT DOCUMENTS

| | | |
|---|---|---|
| GB | 2 157 140 A | 10/1985 |
| JP | 2000-214300 A | 8/2000 |
| JP | 2002-171949 | 6/2002 |
| JP | 2002-171949 A | 6/2002 |

\* cited by examiner

US 7,417,239 B2

METHOD AND DEVICE FOR ELECTRON BEAM IRRADIATION

THE FIELD OF INVENTION

The present invention refers to a device for electron beam irradiation of at least one side of a web and a method of ventilating said device.

PRIOR ART

Within the food packaging industry it has for a long time been used packages formed from a web of packaging material comprising different layers of paper or board, liquid barriers of for example polymers and gas barriers of for example thin films of aluminium. In the packaging machine the web is formed into a tube by overlappingly sealing the longitudinal edges of the web. The tube is continuously filled with a product and then transversally sealed and formed into cushions. The cushions are separated and formed into for example parallelepipedic containers. This technology of forming a tube from a web is well known per se and will not be described in detail.

To extend the shelf-life of the products being packed it is prior known to. sterilise the web before the forming and filling operations. Depending on how long shelf-life is desired and whether the distribution and storage is made in chilled or ambient temperature, different levels of sterilization can be choosen. One way of sterilising a web is chemical sterilization using for example a bath of hydrogen peroxide. Another way is to irradiate the web by electrons emitted from an electron beam emitter. Such an emitter is disclosed in for example U.S. Pat. No. 5,194,742.

There are amongst others two important things that have to be taken into consideration when using an electron beam emitter. The first is how to maintain a desired sterilization level inside the device. A device for web sterilization is formed with openings for the entrance and exit of the web. Unfortunately, bacteria and dirt particles may enter through the openings and also through interconnections between different portions of the device and the surrounding equipment. If these bacteria and dirt particles are left in the device they may recontaminate the web after it has been sterilised.

The second consideration is how to safely discharge ozone ($O_3$) from the device thereby minimising the risk of ozone leakage to the outside of the device. It is common knowledge that the presence of oxygen molecules ($O_2$) in an electron irradiation device give rise to the formation of ozone during electron irradiation because of radical reactions.

SUMMARY OF THE INVENTION

Therefore, an object of the invention has been to provide a device for electron beam irradiation in which both of the above mentioned considerations have been taken into account and solved.

The present invention relates to a method of ventilating a device for electron beam irradiation of at least one side of a web. In accordance with a first aspect of the invention, the method comprises the steps of: providing a first chamber comprising a web inlet opening and a web outlet opening, providing a second chamber extending inside the first chamber, the second chamber comprising a web inlet opening, a web outlet opening, and an electron exit surface through which electrons are adapted to be emitted into the second chamber, passing the web through the second chamber, and creating a flow of a gaseous fluid through both the first and second chambers in a direction opposite the direction of travel of the web by supplying said fluid into the web outlet opening of the first chamber and providing at least one outlet. By providing a flow of gaseous fluid through the device in a direction opposite the direction of travel of the web a desired level of sterilization can be maintained inside the device. Any bacteria or dirt particles entering the device at any point will be transported by the flow to that end of the device where the unsterilised web enters, and there it will be discharged from the device through the outlet. The risk of recontamination of the sterilised web before filling and sealing operations is thereby minimised. Further, ozone ($O_3$) that is formed during irradiation with electrons can be effectively and reliably discharged from both the first and second chambers by the same flow of gaseous fluid. The risk of leakage of ozone to the outside of the device is thereby minimised.

An additional advantage is that the flow of gaseous fluid is suitable for use during pre-sterilization of the device. Hydrogen peroxide can for example be supplied to the gaseous fluid and thereby the surfaces of both the first and second chambers are sterilised.

In accordance with a second aspect of the invention, the method comprises the steps of: providing a first chamber comprising a web inlet opening and a web outlet opening, providing a second chamber extending inside the first chamber, the second chamber comprising a web inlet opening, a web outlet opening, and an electron exit surface through which electrons are adapted to be emitted into the second chamber, passing the web through the second chamber, providing fluid connection between the web outlet opening of the second chamber and the web outlet opening of the first chamber, preventing fluid connection between the first chamber and the web outlet opening of the first chamber, and creating a flow of a gaseous fluid through both the first and second chambers in a direction opposite the direction of travel of the web by supplying said fluid into the first chamber and into the web outlet opening of the first chamber and providing at least one outlet. By providing a flow of gaseous fluid through the device in a direction opposite the direction of travel of the web a desired level of sterilization can be maintained inside the device and the ozone can be safely discharged without leakage to the outside of the device. Further, this design is advantageous if it is desired to have different pressures in the respective chambers since the chambers are supplied by at least one gaseous fluid supply each.

Advantageously, the method comprises the step of providing fluid connection between the web inlet opening of the first chamber and both the first chamber and the web inlet opening of the second chamber. By providing this fluid connection, the gaseous fluid from the first chamber can be discharged from the second chamber, which makes it possible to provide only one outlet.

In a preferred embodiment the method comprises the step of providing fluid connection between the web outlet opening of the first chamber and both the first chamber and the web outlet opening of the second chamber. In this way both chambers may be easily supplied by the same gaseous fluid supply.

In an additional embodiment the web outlet opening of the second chamber is located at a distance from and preferably substantially in line with the web outlet opening of the first chamber. In this way it is not necessary to arrange web guides between the two chambers, and the gaseous fluid that enters through the outlet opening of the first chamber is easily supplied to both chambers.

Preferably, the outlet is provided in vicinity of the web inlet opening of the second chamber. By providing the outlet in an end of the device opposite the web outlet opening any bacteria or dirt particles will be forced to the end of the device where the web has not yet been sterilised, thereby minimising the risk of recontamination once the web has been sterilised.

Advantageously, the outlet is provided inside the second chamber in the vicinity of the web inlet opening. In this way the ozone is not likely to reach the first chamber, which further minimises the risk of leakage to the outside of the device.

In a preferred embodiment, the outlet is provided in the vicinity of the web inlet opening of the first chamber. In this way the discharge can be made in a reliable way with minimised risk of recontamination of the sterilised web.

Preferably, the method comprises the step of controlling the flow of gaseous fluid so that a first overpressure is created inside the first closed chamber, and a second overpressure is created inside the second chamber. By providing overpressure in the first and second chamber, the risk of having bacteria and dirt particles from outside the device entering the chambers is minimised. Thus, the inside of the device can be kept at a desired sterilization level.

In an embodiment the overpressures are chosen so that the first overpressure and the second overpressure are the same. In this way undesired transport of for example ozone or dirt particles between the two chambers is prevented.

In another embodiment the overpressures are chosen so that the first overpressure and the second overpressure are different. For example the first overpressure can be higher than the second overpressure. One reason for choosing such is to keep the ozone within the second chamber where it can be immediately discharged. One reason for choosing the second overpressure so that it is higher than the first overpressure could be to obtain a fast evacuation of ozone and eventual other volatile substances, that for example cause off-flavour, from the second chamber.

The invention also comprises a device for electron beam irradiation of at least one side of a web. The device comprises a first chamber comprising a web inlet opening and a web outlet opening, a second chamber extending inside the first chamber, the second chamber comprising a web inlet opening, a web outlet opening, and being adapted to receive an electron beam emitter provided with an electron exit window through which electrons are adapted to be emitted into the second chamber, the web being adapted to pass the second chamber, and the web outlet opening of the first chamber being adapted to be in communication with a gaseous fluid supply and both chambers being in communication with an outlet, the supply and the outlet are adapted to create a flow of the gaseous fluid through both the first and second chambers in a direction opposite the direction of travel of the web. As explained before, a desired level of sterilization can be maintained inside the device. Further, ozone that is formed during irradiation with electrons can be effectively and reliably discharged from both the first and second chambers. The risk of leakage of ozone to the outside of the device is thereby minimised.

The invention also comprises a device for electron beam irradiation of at least one side of a web, the device comprising a first chamber comprising a web inlet opening and a web outlet opening, a second chamber extending inside the first chamber, the second chamber comprising a web inlet opening, a web outlet opening, and being adapted to receive an electron beam emitter provided with an electron exit window through which electrons are adapted to be emitted into the second chamber, the web being adapted to pass the second chamber, a fluid connection is adapted to be provided between the web outlet opening of the second chamber and the web outlet opening of the first chamber, a fluid connection is adapted to be prevented between the first chamber and the web outlet opening of the first chamber, the web outlet opening of the first chamber being adapted to be in communication with a first gaseous fluid supply, the first chamber being adapted to be in communication with a second gaseous fluid supply, both chambers being in communication with an outlet, and the first and second supplies and the outlet are adapted to create a flow of the gaseous fluid through both the first and second chambers in a direction opposite the direction of travel of the web.

The invention further comprises a device for electron beam irradiation of at least one side of a web, the device comprising a first chamber comprising a web inlet opening and a web outlet opening, a second chamber extending inside the first chamber, the second chamber comprising a web inlet opening, a web outlet opening, and an electron beam emitter provided with an electron exit window through which electrons are to be emitted into the second chamber, the web being adapted to pass the second chamber, and the web outlet opening of the first chamber is in communication with a gaseous fluid supply and both chambers are in communication with an outlet, the supply and the outlet are adapted to create a flow of the gaseous fluid through both the first and second chambers in a direction opposite the direction of travel of the web.

Moreover, the invention also comprises a device for electron beam irradiation of at least one side of a web, the device comprising: a first chamber comprising a web inlet opening and a web outlet opening, a second chamber extending inside the first chamber, the second chamber comprising a web inlet opening, a web outlet opening, and an electron beam emitter provided with an electron exit window through which electrons are emitted into the second chamber, the web being adapted to pass the second chamber, a fluid connection is provided between the web outlet opening of the second chamber and the web outlet opening of the first chamber, the first chamber is prevented from being in fluid connection with the web outlet opening of the first chamber, the web outlet opening of the first chamber being in communication with a first gaseous fluid supply, the first chamber is in communication with a second gaseous fluid supply, both chambers being in communication with an outlet, and the first and second supplies and the outlet are adapted to create a flow of the gaseous fluid through both the first and second chambers in a direction opposite the direction of travel of the web.

BRIEF DESCRIPTION OF THE DRAWINGS

In the following, a presently preferred embodiment of the invention will be described in greater detail, with reference to the enclosed drawings, in which.

DESCRIPTION OF PREFERRED EMBODIMENTS

Figure 1:
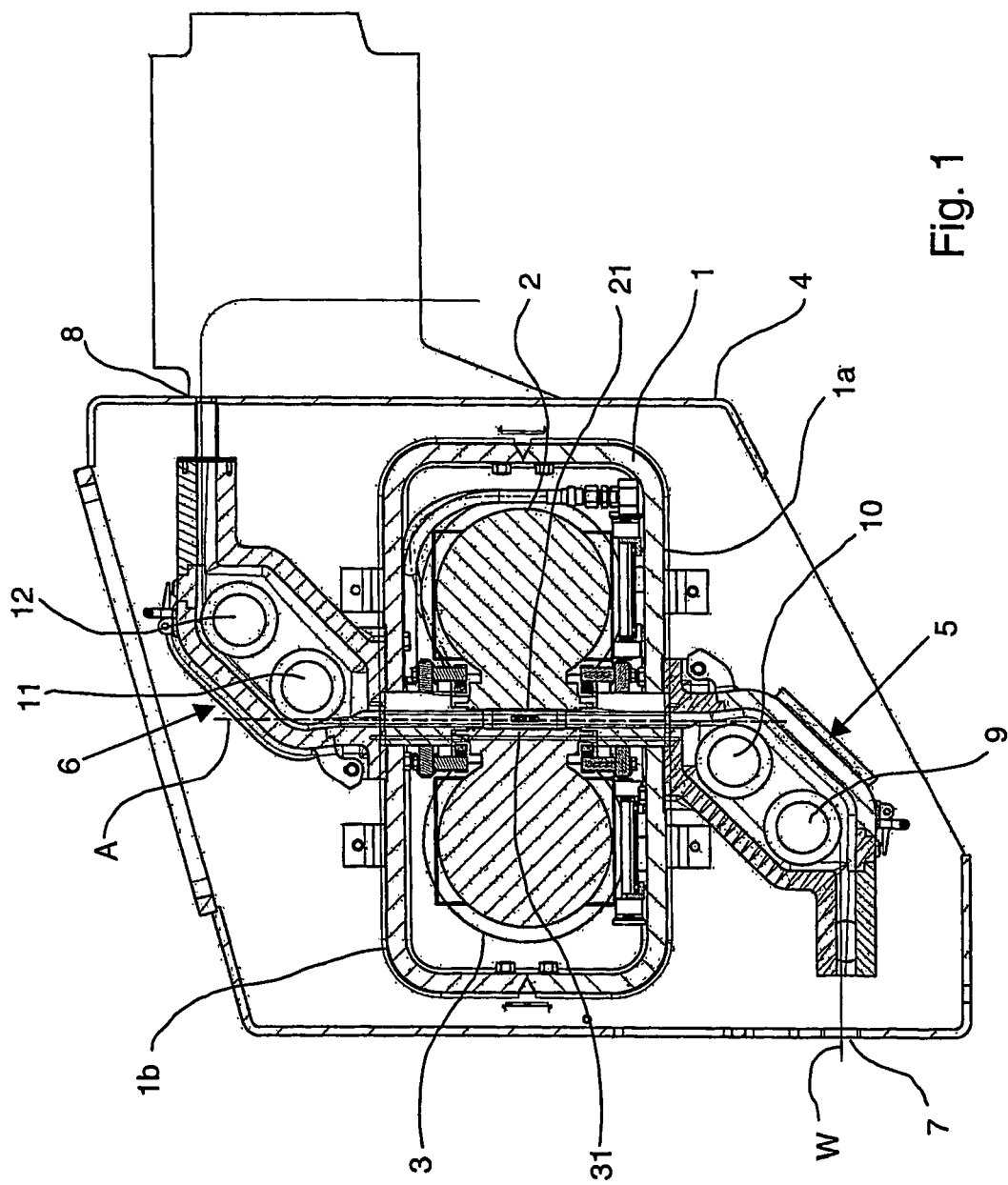
FIG. 1 shows a schematic cross section of the embodiment of the device.
Figure 3:
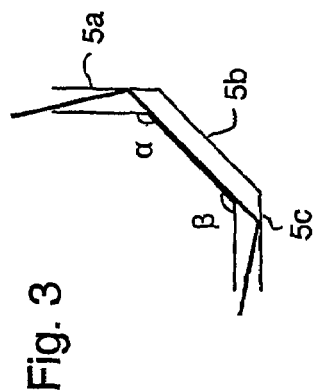
FIG. 3 shows a schematic first illustration on the relation between the tunnel widths, the angles and the lengths of the segments.
Figure 4:
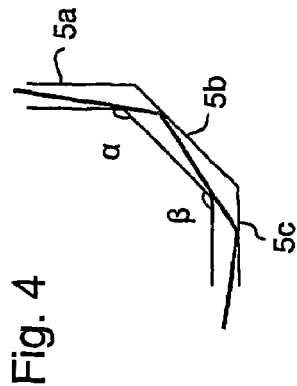
FIG. 4 shows a schematic second illustration on the relation between the tunnel widths, the angles and the lengths of the segments.
Figure 2:
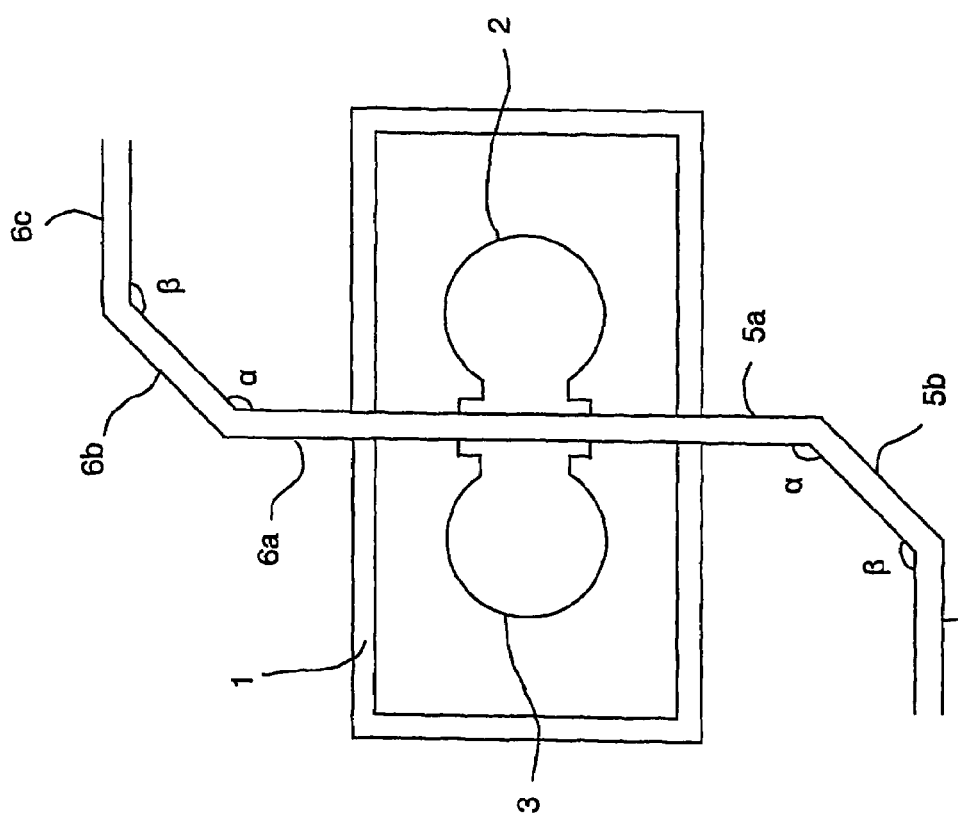
FIG. 2 shows a schematic view illustrating the segments of the tunnel, the angles and the inner housing with the emitters.

The device, shown in FIG. 1, comprises an inner housing 1 in which one or two emitters 2,3 are mounted. A central portion of the inner housing is adapted to receive the emitters. The inner housing 1 forms a tunnel and a packaging material web W is fed through the tunnel past the emitters 2,3. Further, the inner housing 1 is provided with an inlet portion 5 and an outlet portion 6 for the entrance and the exit of the web. The web inlet portion 5 is designed such that the inlet direction of the web W into the inlet portion 5 is angled in relation to the outlet direction of the web W out of the inlet portion 5. The outlet direction of the web W out of the inlet portion 5 is equal to the direction in which the web W passes the emitters 2,3. The angle between the inlet and the outlet direction of the web W in the inlet portion 5 is at least 90°. The inlet portion 5 is formed such that it is angled at at least two locations. In FIG. 2 is shown that the inlet portion 5 comprises three successive segments, an entrance segment 5a, a central segment 5b and an exit segment 5c. The central segment 5b forming a first angle α to the entrance segment 5a and the exit segment 5c forming a second angle β to the central segment 5b. Further, the relation between the tunnel widths, said angles α,β and the lengths of the segments 5a-c is such that an imagined straight line hitting the tunnel wall in the entrance segment 5a also hits the tunnel wall of at least the exit segment 5c, before exiting the exit segment 5c, and that an imagined straight line passing through the entrance segment 5a hits the tunnel wall of the central segment 5b such that it also hits the tunnel wall of at least the exit segment 5c, before exiting the exit segment 5c. In FIG. 3 and 4 are illustrated how the design can be obtained with help of paper, a ruler and a pen. In FIG. 3 a first worst case scenario is disclosed. A straight line is drawn beginning outside the entrace segment 5a and pointing substantially towards the outer corner between the entrance segment 5a and the central segment 5b. The line hits the tunnel wall in the entrance segment 5a and is drawn pointing substantially towards the inner corner between the central segment 5b and the exit segment 5c. If the relation between tunnel widths, angles α,β and segment lengths is to be considered good enough, the straight line will be forced to hit the tunnel wall of the exit segment 5c before exiting the exit segment 5c. In FIG. 4 a second worst case scenario is disclosed. A straight line is now drawn beginning outside the entrace segment 5a and pointing substantially towards the inner corner close to the exit of the entrance segment 5a, but is hitting the tunnel wall in the central segment 5b. The line is then drawn substantially towards the inner corner between the central segment 5b and the exit segment 5c. If the relation between tunnel widths, angles α,β and segment lengths is to be considered good enough, the straight line will be forced to hit the tunnel wall of the exit segment 5c before exiting the exit segment 5c. Thus, it is realised that if a certain angle is used, the parameters that can be modified are either the tunnel width or the length of the segment. A wide tunnel necessitates a long segment. If there is a need for a short segment, the tunnel width must be decreased. Another possibility is of course to change one or both of the angles.

The change in the running direction of the web W is accomplished by providing the inlet portion 5 with at least one web guide. In the example the web guide is a first and a second roller 9, 10 mounted inside the inlet portion 5. In the disclosed design the web W runs substantially horizontal into the inlet portion 5 and substantially vertically upwards when it leaves the inlet portion 5 and enters the inner housing 1. To accomplish this change in direction the rollers 9, 10 being formed and mutually located in such a way that the first roller 9 angles the web W the second angle β and that the second roller 10 angles the web W the first angle α. Preferably, the rollers 9, 10 are journalled in support members. The support members can for example be bearings provided with an outer shielding or with a bearing housing designed following the same design criteria as the tunnel.

The outlet portion 6 is similarly designed with an entrance segment 6a, a central segment 6b and an exit segment 6c. To change the running direction of the web W the outlet portion 6 comprises one or more rollers 11, 12. The inlet portion 5 and the outlet portion 6 are mounted and designed such that the web W runs in the same direction as it leaves the outlet portion 6 as it does as it enters the inlet portion 5. In the disclosed design the inlet portion 5 and the outlet portion 6 are identical and mounted to two opposite faces 1a, 1b of the inner housing 1 using the same flange on respective portion 5, 6 but turned 180° about an axis A extending along the centre line of the web W running through the inner housing 1. Thus, the respective entrance segment 5a, 6a of the inlet portion 5 and the outlet portion 6 are adjacent the central portion of the tunnel and that the respective exit segment 5c, 6c of the inlet portion 5 and the outlet portion 6 are directed away from each other.

An outer housing 4 surrounds the inner housing 1 and the outer housing 4 is provided with openings forming an inlet 7 and an outlet 8 for the entrance and the exit of the web W.

Figure 5:
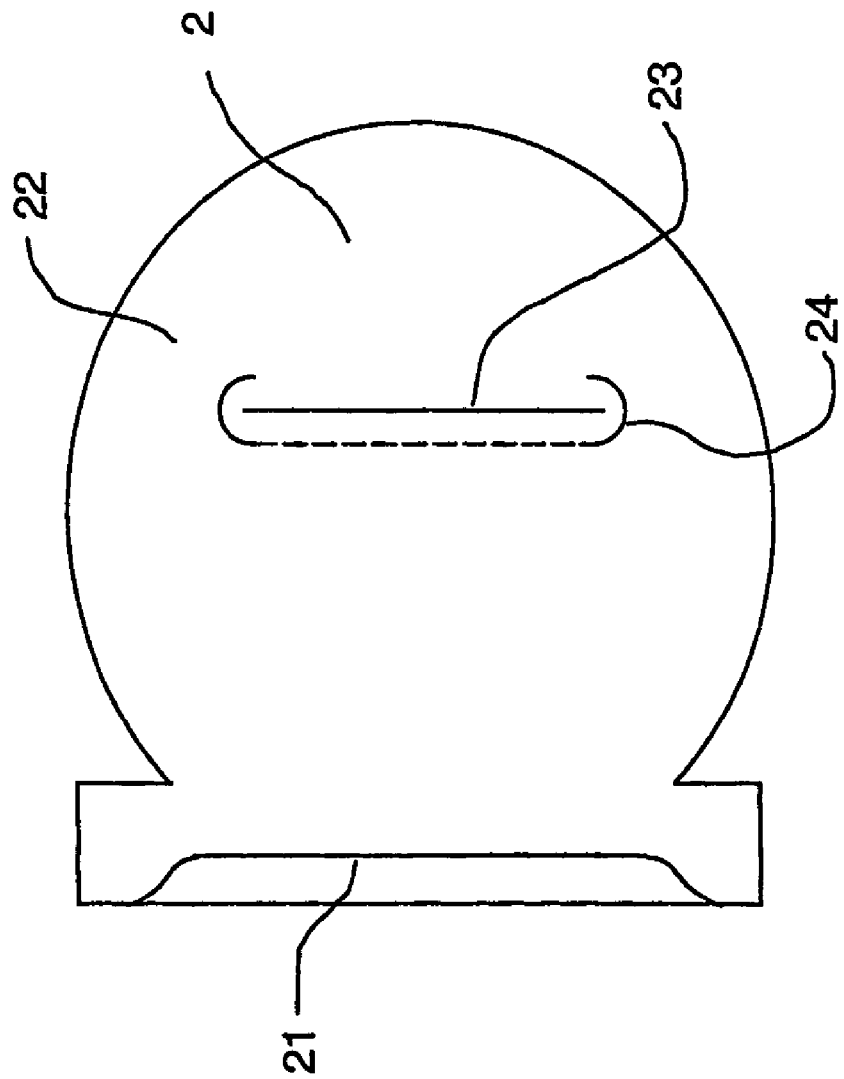
FIG. 5 shows a schematic cross section of an emitter enclosed in the device.

The emitters 2, 3 transmit an electron beam out through the exit windows 21, 31. One side of the web W is irradiated by the first emitter 2 and the other side is irradiated by the second emitter 3. For this purpose the second electron beam emitter 3 is positioned substantially opposite the first emitter 2 and the electron exit window 31 of the second emitter 3 is positioned substantially opposite the first electron exit window 21. Below only one emitter 2 will be described in more detail. In accordance with the disclosed design, shown in FIG. 5, the emitter 2 generally comprises a vacuum chamber 22 in which a filament 23 and a cage 24 is provided. The filament 23 is made of tungsten. When an electrical current is fed through the filament 23, the electrical resistance of the filament 23 causes the filament 23 to be heated to a temperature in the order of 2000° C. This heating causes the filament 23 to emit a cloud of electrons. A cage 24 provided with a number of openings surrounds the filament 23. The cage 24 serves as a Faraday cage and help to distribute the electrons in a controlled manner. The electrons are accelerated by a voltage between the cage 24 and the exit window 21. The emitters used are generally denoted low voltage electron beam emitters, which emitters normally have a voltage below 300 kV. In the disclosed design the accelerating voltage is in the order of 70-85 kV. This voltage results in a kinetic (motive) energy of 70-85 keV in respect of each electron. The electron exit window is substantially planar and provided substantially in parallell with the web. Further, the exit window 21 is made of a metallic foil and has a thickness in the order of 6 μm. A supporting net formed of aluminium supports the exit window 21. An emitter of this kind is described in more detail in U.S. Pat. No. 6,407,492B1. In U.S. Pat. No. 5,637,953 is another emitter disclosed. This emitter generally comprises a vacuum chamber with an exit window, wherein a filament add two focusing plates are provided within the vacuum chamber. In U.S. Pat. No. 4,910,435 is yet another emitter disclosed, wherein the electrons are emitted by secondary emittance from a material bombarded by ions. Reference is made to the above patents for a more detailed description of these different emitters. It is contemplated that these emitters and other emitters can be used in the described system.

As long as the electrons are within the vacuum chamber, they travel along lines defined by the voltage supplied to the cage 24 and the window, but as soon as they exit the emitter through the emitter window they start to move in more or less irregular paths (scatter). The electrons are slowed down as they collide with amongst others air molecules, bacteria, the web and the walls of the housing. This decrease of the speed of the electrons, i.e. a loss in kinetic energy, gives rise to the emission of X-rays (roentgen rays) in all directions. The X-rays propagate along straight lines. When such an X-ray hits the inner wall of the housing, the X-ray enters a certain distance into the material and causes emittance of new X-rays in all directions from the point of entrance of the first X-ray. Every time an X-ray hits the wall of the housing and gives rise to a secondary X-ray, the energy is about 700-1000 times less, dependent upon the choice of material for the housing. Stainless steel has a reduction ratio of about 800, i.e. the energy of a secondary X-ray is reduced about 800 times in relation to the primary X-ray. Lead is a material often being considered when radiation is involved. Lead has a lower reduction ratio, but has on the other hand a higher resistance against transmission of the X-rays through the material. If the electrons are accelerated by a voltage of about 80 kV, they are each given a kinetic energy of about 80 keV. In order to secure that the X-rays of this energy level do not pass through the inner housing 1, the inner housing 1 is made of stainless steel having a thickness of 22 mm. This thickness is calculated for X-rays travelling perpendicular to the wall. An X-ray travelling inclined in relation to the wall will experience a longer distance in the wall to reach the same depth, i.e. the wall will appear thicker. The wall thickness is determined by the governmental regulations concerning amount of radiation outside the housing. Today the limiting value that the radiation must be less than is 0.1 µSv/h measured at a distance of 0.1 m form any accessible surface, i.e outside shielding. It should be noted that the choice of material and the dimensions are influenced by the regulations presently applicable and that new regulations might alter the choice of material or the dimensions. The energy of each electron (80 keV) and the number of electrons determine the total energy of the electron cloud. This total energy results in a total energy transfer to the surface to be sterilized. This radiation energy is measured in the unit Gray (Gy). In case of the electron emitter briefly described above (with a filament and Faraday cage) it is presently considered suitable to use a current of about 17 mA through the filament. This is however dependent upon the radiation level decided and the area of the surface to be sterilised. In the present example it is contemplated to sterilise a web with a width of 400 mm travelling with a speed of 35 m/s past the emitter. This will give a radiation energy in the order of 35 kGy on average. In another example the web width is still 400 mm, but the speed that the web is travelling with is increased to 100 m/s. To obtain the same radiation energy, 35 kGy, the current is increased to approximately 50 mA.

In the following the gaseous fluid system of the device will be described. In this embodiment the fluid is air, but it can of course be any gaseous fluid suitable for the field of application in which the device is used.

Figure 6:
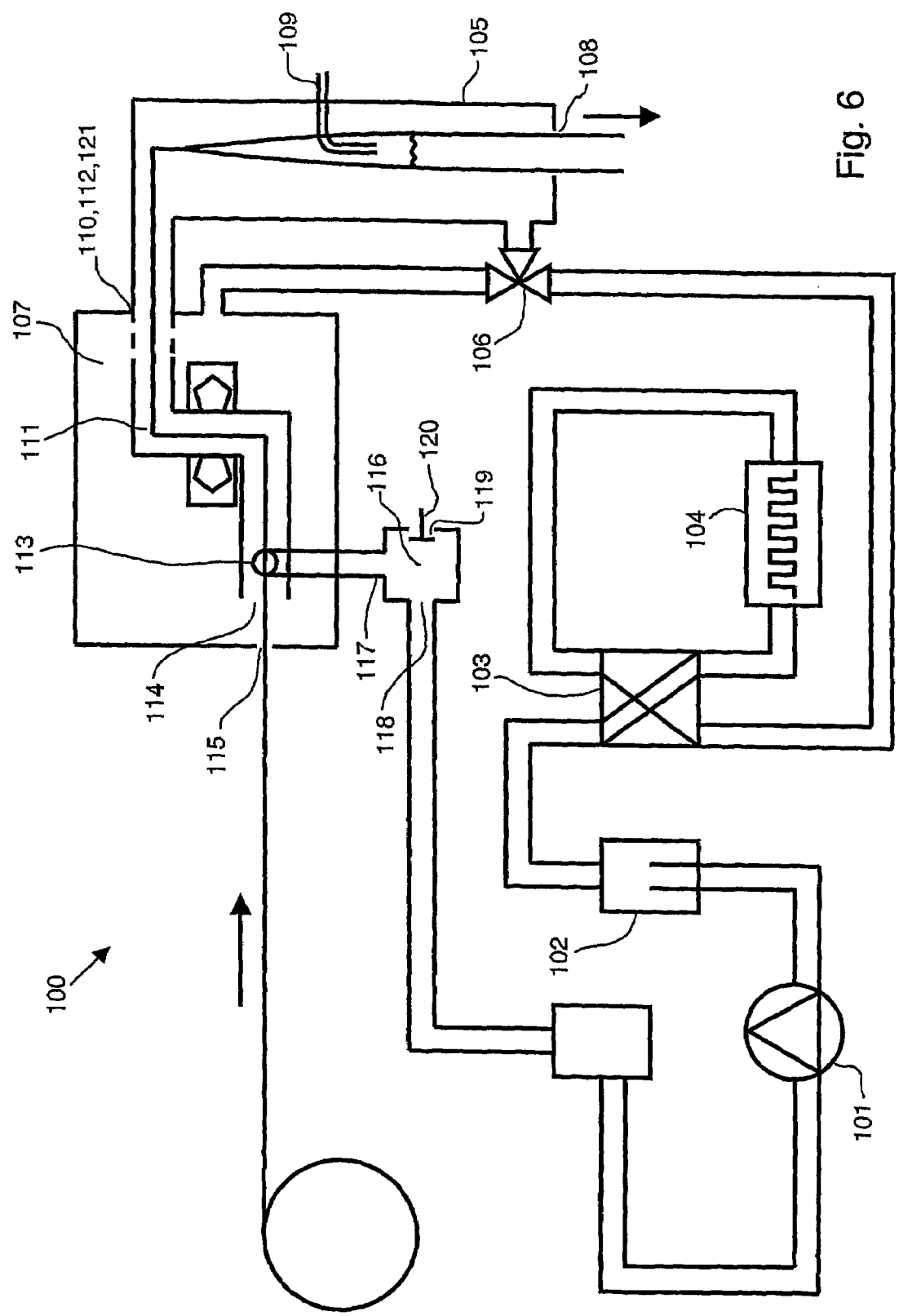
FIG. 6 shows a schematic view of the air system according to the invention.

The air system 100 of the machine, shown in FIG. 6, comprises a compressor 101 and a water separator 102 from which pressurised air is obtained. This air is supplied to a heat exhanger 103 in which the air is pre-heated to about 100° C. From the heat exhanger 103, the air is fed to a superheater 104 in which the air is heated to a temperature within the range 330-450° C. At temperatures above 330° C. any bacteria in the air is killed. The killing rate is dependent upon the temperature and the time the bacteria are subjected to said temperature. The air from the superheater 104 is returned to the heat exhanger 103 for achieving the above-described pre-heating of the incoming air. After the second passage through the heat exchanger 103, the air has a temperature of about 90° C. The air is then fed to a change-over valve 106 having a first branch in fluid connection with the tower 105 of the filling machine and a second branch in fluid connection with a first chamber 107 formed by the outer housing 4. A small amount of the air supplied to the tower 105 will follow the web W out of the tower 105 through an outlet opening 108. In the tower 105 the web W is formed into a tube by overlappingly sealing the longitudinal edges of the web. The tube is continuously filled with a product via a product pipe 109 extending into the tube from the end where the web W has not yet been transformed into a tube. This technology of forming a tube from a web is well known per se and will not be described in detail. The outlet opening 108 is provided with a sealing ring (not shown) in order to have a controlled flow of air out of the outlet opening 108. This can also be achieved by forming the outlet opening 108 with a given clearance in respect of the tube being fed out through the opening 108. The tube is transversally sealed and formed into cushions, which are separated and formed into parallelepipedic containers. Again, this technology is well known per se and will not be described in detail. A significant portion of the air supplied to the tower 105 flows in the tower 105 in a direction opposite the direction of travel of the web W. The tower 105 is provided with a web inlet opening 110 acting as an air outlet opening 110. The air from the tower 105 is fed to a second chamber 111 formed of the inner housing 1.

In the following the area marked with dashed lines in FIG. 6 will be described. The dashed lines represent two alternative embodiments of the air flow into the first and second chambers. In a first embodiment the lines are continuous and represents a closed communication directly between a web outlet opening 112 of the second chamber 111 and a web outlet opening 121, also denoted outlet 8, of the first chamber 107. In a second embodiment the lines are not present and represents an open communication between both the first and second chambers 107, 111 and the web outlet opening 121 of the first chamber 107.

In the first embodiment there is provided a fluid connection between a web outlet opening 112 of the second chamber 111 and a web outlet opening 121 of the first chamber 107. Thus, the air is fed into the second chamber 111 via the web outlet opening 112 acting as an airflow inlet opening 112. The tower 105 acting as a first air supply. If the web outlet opening 112 of the second chamber 111 is located at a distance from and preferably substantially in line with the web outlet opening 121 of the first chamber 107, the fluid connection can for example comprise a pipe that connects the web outlet opening 112 of the second chamber 111 with the web outlet opening 121 of the first chamber 107. Alternatively, the web outlet opening 112 of the second chamber 111 extends to the web outlet opening 121 of the first chamber 107. A fluid connection between the first chamber 107 and the web outlet opening 121 of the first chamber 107 is thereby prevented. As been earlier described, the change-over valve 106 is acting as air supply 106 for the first chamber 107.

In a second embodiment both the first chamber 107 and the second chamber 111 are in fluid connection with the web outlet opening 121 of the first chamber 107, thus both chambers 107, 111 being in connection with the air supply in the tower 105. In addition, the first chamber 107 is being in contact with valve 106 for additional supply of air.

In both embodiments the air in the second chamber 111 flows in a direction opposite the direction of travel of the web W through the second chamber 111. After passage almost completely through the second chamber 111 the air is fed via a discharge outlet 113 for ultimate disposal of the air. Similarly, the air provided to the first chamber 107 flows in a direction opposite the direction of travel of the web W. The air from the first chamber 107 and the second chamber 111 is discharged via the outlet 113. Thus, both chambers 107, 111 being in contact with the outlet. A small amount of the air supplied to the first chamber 107 escapes via a web inlet opening 115, also denoted inlet 7. The amount escaping is dependent of the shape of the gap and the sealing used. This in turn depend amongst others upon if the web is supplied with pre-applied opening devices or not.

Figure 7:
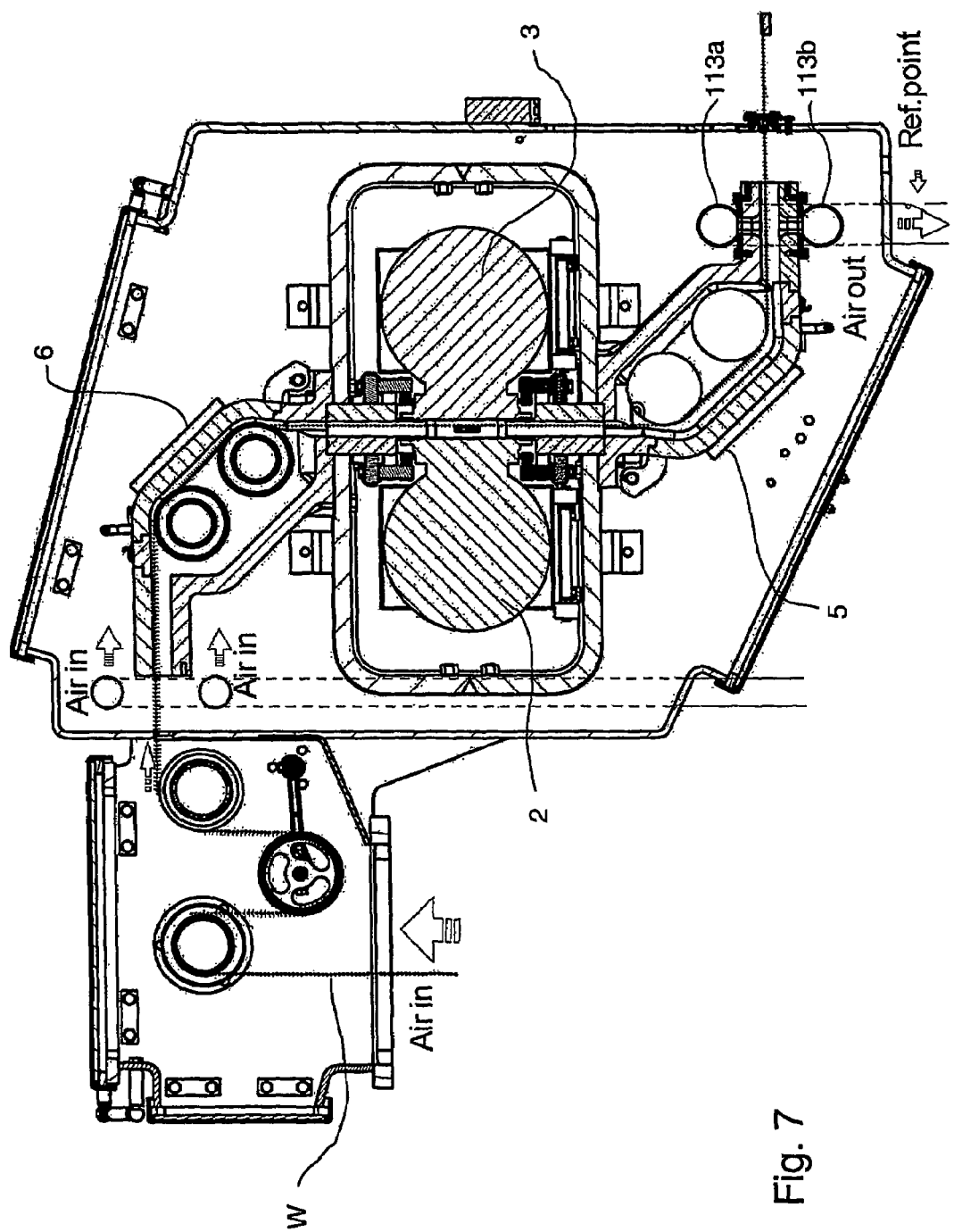
FIG. 7 shows a schematic view like FIG. 1, but shown from the other side and which shows an alternative embodiment.

The discharge outlet 113 is located close to the web inlet opening 114 of the second chamber 111. In FIG. 1, the outlet 113 is located inside the second chamber 111. For example the outlet 113 can be located in the vicinity of the web inlet opening 114 of the second chamber 111. The outlet 113 is discharging almost all the air from the second chamber 111 and most of the air from the first chamber 107. There is provided a fluid connection between the web inlet opening 115 of the first chamber 107 and both the first chamber 107 and the web inlet opening 114 of the second chamber 111. In an alternative embodiment shown in FIG. 7 the outlet 113 comprises two branches 113a, 113b in fluid connection with the second chamber 111. With reference to the figure, the first outlet branch 113a is located in the top of the chamber wall in the vicinity of the web inlet opening 114 of the second chamber 111, and the second outlet branch 113b is located in the bottom wall opposite the first.

The flow of air in the system is controlled so that a first overpressure is created inside the first chamber 107. In the described embodiment the pressure is in the order of 30 mm $H_2O$. Further, a second overpressure is created inside the second chamber 111. The overpressures can for example be choosen so that the first overpressure and the second overpressure are the same. Alternatively, the overpressures are choosen so that the first overpressure and the second overpressure are different. The first pressure can be higher than the second pressure and vice versa. One reason for choosing the first overpressure so that it is higher than the second overpressure is to keep ozone ($O_3$), formed during irradiation, within the second chamber 111 where it can be immediately discharged through the outlet 113. Further, a lower second overpressure helps during pre-sterilization of the device at for example start-up of the machine. By having a lower pressure in the second chamber compared to the first chamber, a sufficient amount of the hydrogen peroxide used during the sterilization is forced inside the second chamber. The pre-sterilization will be explained in more detail below. One reason for choosing the second overpressure so that it is higher than the first overpressure could be to obtain a fast evacuation of ozone and eventual other volatile substances, that for example cause off-flavour, from the second chamber.

Inside the inner housing 1, i.e. around the emitters 2,3, is provided a pressure that is preferably lower than the pressure inside the second chamber 111. One reason for choosing a pressure lower than the pressure inside the second chamber 111 is to minimise the risk of recontamination of the web W by contaminated air contained in the inner housing 1. Since no certain pressure is necessary for the emitters 2, 3 used in this particular embodiment, the pressure in the inner housing 1 can be atmospheric pressure. However, it should be understood that the inner housing 1 may be pressurised if necessitated by the emitters used.

Outside the first chamber 107, the air system 100 is provided with a so-called zero point 116. The zero point 116 is a device making sure that if something fails in the system, any air needed to avoid a pressure below the atmospheric pressure will be fed into the system via the zero point 116. This way it is secured that the pressure inside the tower 105, the first chamber 107 and the second chamber 111 at least not will drop below the atmospheric pressure. The zero point 116 generally comprises a housing with an inlet 117 and an outlet 118 and an opening 119 being closed by a valve 120. Any pressure above the atmospheric pressure pushes the valve outwards sealingly closing of the opening 119. If the pressure inside the zero point 116 drops below the atmospheric pressure the valve 120 will not be pushed against the opening 119 (on the contrary it will be pushed inwards into the zero point 116 and air can be introduced into the system via the opening 119).

During for example start-up of the machine, the air system 100 can be used for sterilizing the surfaces inside of tower 105 and the chambers 107,111 prior to entering the web W. The sterilization is made with hydrogen peroxide ($H_2O_2$). Sterilization using hydrogen peroxide is known per se, but will be briefly described in the following with regard to the air system 100. The tower 105 is in connection with a hydrogen peroxide supply, which is provided with aerosol nozzles. The nozzles feed hydrogen peroxide into the air as spray and the air supplied in the tower is heated to a temperature at which the hydrogen peroxide vapourises, normally a temperature in the order of 40-50° C. The hydrogen peroxide contained air flows through the tower and the chambers 107,111 in the arlier described direction and is discharged at the discharge outlet 113. Along he way the hydrogen peroxide condenses on the surfaces. The hydrogen peroxide is then removed from the surfaces by supplying air of a temperature at or above the hydrogen peroxide vapourisation temperature. In this embodiment a temperature in the order of 70-90° C. is used. By providing a temperture well above the vaporisation temperature the hydrogen peroxide is effectively and quickly removed from the surfaces.

In accordance with the method for electron beam irradiation of a web W, the web W is provided to pass through the tunnel. The tunnel is being provided with a web inlet portion 5, a web outlet portion 6 and a central portion adapted to receive an electron beam emitter 2, 3 provided with an electron exit window 21, 31. Electrons are emitted into the tunnel from the emitter 2,3 through the electron exit window 21, 31, and any X-ray being formed by the electrons during irradiation of the web W is forced to hit the tunnel wall twice before exiting the tunnel. To accomplish at least two hits the tunnel is being formed angled at at least two locations in each of the inlet and outlet portions 5, 6.

Further, the method comprises forming the inlet portion 5 so that it comprises a line of three sucsessive segments, an entrance segment 5a, a central segment 5b and an exit segment 5c. The central segment 5b is made so that it forms a first angle α to the entrance segment 5a. Furthermore, the exit segment 5c forms a second angle β to the central segment 5b. The outlet portion 6 is similarly designed.

A relation between the tunnel widths, said angles α,β and the lengths of the segments 5a-c is formed so that an imagined straight line hitting the tunnel wall in the entrance segment 5a is also hitting the tunnel wall of at least the exit segment 5c, before exiting the exit segment 5c, and that an imagined straight line passing through the entrance segment 5a is hitting the tunnel wall of the central segment 5b such that it is also hitting the tunnel wall of at least the exit segment 5c, before exiting the exit segment 5c.

It is known that during irradiation with electrons ozone ($O_3$) is formed inside the device. Therefore, the invention also comprises a method of ventilating the device. The method comprises the step of providing a first chamber 107 comprising a web inlet opening 115 and a web outlet opening 121. The first chamber 107 being the outer housing 4. A second chamber 111, being the tunnel, is also provided and extends inside the first chamber 107. The second chamber 111 is formed comprising a web inlet opening 114 and a web outlet opening 112. Further, an electron exit window 21, 31 is provided through which electrons are adapted to be emitted into the second chamber 111. The web W is passing through the second chamber 111, and a flow of air through both the first and second chambers 107, 111 is created. The air flow flows in a direction opposite the direction of travel of the web W. The air is supplied into the web outlet opening 121 of the first chamber 107 and there is provided at least one outlet 113.

In an alternative method fluid connection is being provided between the web outlet opening 121 of the second chamber 111 and the web outlet opening 112 of the first chamber 107. At the same time fluid connection between the first chamber 107 and the web outlet opening 121 of the first chamber 107 is prevented. A flow of air through both the first and second chambers 107, 111 in a direction opposite the direction of travel of the web W can then be created by supplying said air into the first chamber 107 and into the web outlet opening 121 of the first chamber 107 and providing at least one outlet 113. Air is supplied to the first chamber 107 through a valve 106 being in fluid connection with the first chamber 107.

According to the method the web W is thus entering the device through the web inlet opening 115 of the first chamber 107 and enters the second chamber 111 at its web inlet opening 114. Both openings 115, 114 are located such that the web W is kept straight, substantially horizontal when passing them. Inside the inlet portion 5 the web W is angled the second angle β at the first roller 9 and angled the first angle α at the second roller 10. During travelling, the web W meets an airflow flowing in a direction opposite the web W. When the web W passes the central portion of the tunnel, now travelling in a vertical direction, it passes electron exit windows 21, 31 through which the web W is irradiated by emitters 2, 3. The electron exit windows 21, 31 are located on opposite sides of the tunnel thereby irradiating both sides of the web W. After the irradiation the web W enters into the outlet portion 6 in which it is angled twice like in the inlet portion 5. Finally, it is exiting the device through the web outlet opening 112 of the second chamber 111, and then through the web outlet opening 121 of the first chamber 107, thereby entering the tower 105.

Although the present invention has been described with respect to a presently preferred embodiment, it is to be understood that various modifications and changes may be made without departing from the object and scope of the invention as defined in the appended claims.

The described embodiment comprises two emitters 2,3, one for electron irradiation of one side of the web W and the other for electron irradiation of the other side of the web W. However, it is to be understood that the device does not need to comprise two emitters 2,3, but can comprise only one emitter. Further, it has been described that the two emitters 2,3 are located opposite each other. Alternatively they can be located at a distance from each other in the web direction.

Moreover, it is also to be understood that the number of emitters can be more than two. It is for example possible to have several emitters side by side to handle wide webs. It is also possible to have two or more emitters located after each other along the direction of the web to form either subsequent sterilizing zones which together provide the decided radiation level, or as measure of selective radiation of a certain point, for example a closure device, that may need a higher radiation level.

Further, it should be understood that the location of the outlet 113 can be modified. In the above-described embodiment the outlet 113 is located inside the second chamber 111. Alternatively the outlet 113 can for example be located in vicinity of the web inlet opening 114 of the second chamber 111 or in the vicinity of the web inlet opening 115 of the first chamber 107. It is also possible to locate the outlet 113 outside, near the inlet opening 115, of the first chamber 107.

Moreover, in the above-described embodiment the outlet 113 is located inside the second chamber 111 and the first chamber 107 is in fluid connection with the second chamber 111. In an alternative embodiment the web inlet opening 114 of the second chamber 111 is in fluid connection with the web inlet opening 115 of the first chamber 107, while fluid connection between the first chamber 107, its web inlet opening 115 and the web inlet opening 114 of the second chamber 111 is prevented. The two chambers 107,111 will then be in communication with separate outlets. At least one outlet can be located in the first chamber 107 and at least one outlet can be located in the second chamber 111 or in fluid connection with the second chamber 111.

Further, the air system described using hydrogen peroxide is preferably used in aseptic fields of application. In a corresponding air system in a packaging machine used for handling pasteurized products the air flows are similar, although the machine sterilization is usually made by using filtered air. Instead of the above described system, the system can then comprise a filter and a fan. To evacuate ozone from the chambers during operation, the system can be provided with a catalytic converter.

Moreover, in the embodiment shown the web inlet opening 114 of the second chamber 111 is located at a distance from and preferably in line with the web inlet opening 115 of the first chamber 107. Alternatively, the second chamber 111 can extend all the way up to the web inlet opening 115 of the first chamber thereby preventing fluid connection between the first chamber 107 and the web inlet opening 115. The wall of the second chamber 111 is then instead provided with throughgoing openings, preferably slits, at a distance from the web inlet opening, but before the outlet 113. Fluid connection between the two chambers is thereby provided and the arrangement give rise to a so called injector effect making air flow from the first chamber through the slits into the second chamber where it can be evacuated through the outlet 113. A small amount of air is also sucked from outside the housings through the web inlet opening 115.

The invention claimed is:

1. Method of ventilating a device for electron beam irradiation of at least one side of a web, the device for electron beam irradiation being comprised of a first chamber and a second chamber, the second chamber extending inside the first chamber in separated relation to the first chamber, the first chamber comprising a web inlet opening and a web outlet opening, the second chamber comprising a web inlet opening, a web outlet opening, and an electron exit surface through which electrons are adapted to be emitted into the second chamber, the method comprising:

passing the web through the second chamber,
   creating a flow of a gaseous fluid through both the first and second chambers in a direction opposite the direction of travel of the web by supplying said fluid into the web outlet opening of the first chamber, and
   discharging the gaseous fluid in at least the second chamber through at least one discharge outlet.

2. Method of ventilating a device for electron beam irradiation of at least one side of a web, the device for electron beam irradiation being comprised of a first chamber and a second chamber, the second chamber extending inside the first chamber in separated relation to the first chamber, the first chamber composing a web inlet opening and a web outlet opening, the second chamber comprising a web inlet opening, a web outlet opening, and an electron exit surface through which electrons are adapted to be emitted into the second chamber, the method comprising:

passing the web through the second chamber, providing fluid connection between the web outlet opening of the second chamber and the web outlet opening of the first chamber, preventing fluid connection between the first chamber and the web outlet opening of the first chamber, creating a flow of a gaseous fluid through both the first and second chambers in a direction opposite the direction of travel of the web by supplying said fluid into the first chamber and into the web outlet opening of the first chamber, and discharging the gaseous fluid in at least the second chamber through at least one discharge outlet.

3. The method according to claim 1, comprising fluidly connecting the web inlet opening of the first chamber and both the first chamber and the web inlet opening of the second chamber.

4. The method according to claim 1, comprising fluidly connecting the web outlet opening of the first chamber and both the first chamber and the web outlet opening of the second chamber.

5. The method according to claim 1, wherein the web outlet opening of the second chamber is located at a distance from and substantially in line with the web outlet opening of the first chamber.

6. The method according to claim 1, wherein the discharge outlet is located in vicinity of the web inlet opening of the second chamber.

7. The method according to claim 1, wherein the discharge outlet is located inside the second chamber in the vicinity of the web inlet opening.

8. The method according to claim 1, wherein the discharge outlet is located in the vicinity of the web inlet opening of the first chamber.

9. The method according to claim 1, comprising controlling the flow of gaseous fluid so that a first overpressure is created inside the first chamber, and a second overpressure is created inside the second chamber.

10. The method according to claim 9, whereby the overpressures are chosen so that the first overpressure and the second overpressure are the same.

11. The method according to claim 9, whereby the overpressures are chosen so that the first overpressure and the second overpressure are different.

12. Device for electron beam irradiation of at least one side of a web, the device comprising:

a first chamber comprising a web inlet opening and a web outlet opening, a second chamber extending inside the first chamber in separated relation to the first chamber, the second chamber comprising a web inlet opening, a web outlet opening, and being adapted to receive an electron beam emitter provided with an electron exit window through which electrons are adapted to be emitted into the second chamber, the web being adapted to pass the second chamber, and the web outlet opening of the first chamber being adapted to be in communication with a gaseous fluid supply and both chambers being in communication with an outlet, the supply and the outlet are adapted to create a flow of the gaseous fluid through both the first and second chambers in a direction opposite the direction of travel of the web.

13. Device for electron beam irradiation of at least one side of a web, the device comprising:

a first chamber comprising a web inlet opening and a web outlet opening, a second chamber extending inside the first chamber in separated relation to the first chamber, the second chamber comprising a web inlet opening, a web outlet opening and being adapted to receive an electron beam emitter provided with an electron exit window through which electrons are adapted to be emitted into the second chamber, the web being adapted to pass the second chamber, a fluid connection is adapted to be provided between the web outlet opening of the second chamber and the web outlet opening of the first chamber, a fluid connection is adapted to be prevented between the first chamber and the web outlet opening of the first chamber, the web outlet opening of the first chamber being adapted to be in communication with a first gaseous fluid supply, the first chamber being adapted to be in communication with a second gaseous fluid supply, both chambers being in communication with a discharge outlet through which is discharged the gaseous fluid from at least one of the first and second gaseous fluid supplies, and the first and second supplies and the discharge outlet are adapted to create a flow of the gaseous fluid through both the first and second chambers in a direction opposite the direction of travel of the web.

14. Device for electron beam irradiation of at least one side of a web, the device comprising:

a first chamber comprising a web inlet opening and a web outlet opening, a second chamber extending inside the first chamber in separated relation to the first chamber, the second chamber comprising a web inlet opening, a web outlet opening, and an electron beam emitter provided with an electron exit window through which electrons are to be emitted into the second chamber, the web being adapted to pass through the second chamber, and the web outlet opening of the first chamber is in communication with a gaseous fluid supply and both chambers are in communication with a discharge outlet through which the gaseous fluid in the chambers is discharged, the supply and the discharge outlet are adapted to create a flow of the gaseous fluid through both the first and second chambers in a direction opposite the direction of travel of the web.

15. Device for electron beam irradiation of at least one side of a web, the device comprising:

a first chamber comprising a web inlet opening and a web outlet opening, a second chamber extending inside the first chamber in separated relation to the first chamber, the second chamber comprising a web inlet opening, a web outlet opening, and an electron beam emitter provided with an electron exit window through which electrons are emitted into the second chamber, the web being adapted to pass through the second chamber, a fluid connection is provided between the web outlet opening of the second chamber and the web outlet opening of the first chamber, the first chamber is prevented from being in fluid connection with the web outlet opening of the first chamber, the web outlet opening of the first chamber being in communication with a first gaseous fluid supply, the first chamber is in communication with a second gaseous fluid supply, both chambers being in communication with a discharge outlet through which the gaseous fluid in the chambers is discharged, and the first and second supplies and the discharge cutlet are adapted to create a flow of the gaseous fluid through both the first and second chambers in a direction opposite the direction or travel of the web.

16. The method according to claim 1, wherein the first chamber through which the flow of The gaseous fluid is created is located inside an outer housing, and the second chamber through which the gaseous flow is created is located inside an inner housing which is separate from and positioned inside the outer housing, the first chamber being between the outer housing and the inner housing.

17. The device according to claim 12, wherein the first chamber is located inside an outer housing, and the second chamber is located inside an inner housing which is separate from and positioned inside the outer housing, the first chamber being between the outer housing and the inner housing.

18. The device according to claim 13, wherein the first chamber is located inside an outer housing, and the second chamber is located inside an inner housing which is separate from and positioned inside the outer housing, the first chamber being between the outer housing and the inner housing.

19. The device according to claim 14, wherein the first chamber is located inside an outer housing, and the second chamber is located inside an inner housing which is separate from and positioned inside the outer housing, the first chamber being between the outer housing and the inner housing.

20. The device according to claim 15, wherein the first chamber is located inside an outer housing, and the second chamber is located inside an inner housing which is separate from and positioned inside the outer housing, the first chamber being between the outer housing and the inner housing.

* * * * *